(12) United States Patent
Shank et al.

(10) Patent No.: US 9,005,695 B2
(45) Date of Patent: Apr. 14, 2015

(54) COMPOSITE STENT WITH INNER AND OUTER STENT ELEMENTS AND METHOD OF USING THE SAME

(71) Applicant: Boston Scientific Scimed, Inc., Maple Grove, MN (US)

(72) Inventors: Peter J. Shank, Boylston, MA (US); Sheng-Ping Zhong, Shrewsbury, MA (US); Kinh-Luan D. Dao, Randolph, MA (US); F. Anthony Headley, Jr., Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 6 days.

(21) Appl. No.: 13/887,886

(22) Filed: May 6, 2013

(65) Prior Publication Data

US 2013/0243937 A1    Sep. 19, 2013

Related U.S. Application Data

(63) Continuation of application No. 10/962,567, filed on Oct. 13, 2004, now Pat. No. 8,435,285, which is a continuation-in-part of application No. 10/720,176, filed on Nov. 25, 2003, now abandoned.

(51) Int. Cl.
*A61L 33/00* (2006.01)
*A61F 2/82* (2013.01)
*A61F 2/07* (2013.01)
*A61F 2/86* (2013.01)
*A61L 31/12* (2006.01)
(Continued)

(52) U.S. Cl.
CPC ... *A61F 2/82* (2013.01); *A61F 2/07* (2013.01); *A61F 2/86* (2013.01); *A61F 2002/075* (2013.01); *A61F 2250/0067* (2013.01); *A61L 31/129* (2013.01); *A61L 31/146* (2013.01); *B05D 1/002* (2013.01); *A61F 2/90* (2013.01); *A61F 2210/0076* (2013.01); *A61F 2220/0008* (2013.01); *A61F 2220/0041* (2013.01); *A61F 2220/005* (2013.01); *A61F 2220/0066* (2013.01); *A61F 2220/0075* (2013.01)

(58) Field of Classification Search
USPC ............... 623/1.44, 1.13, 6, 12, 1, 1.42, 1.46; 424/450
See application file for complete search history.

(56) References Cited

U.S. PATENT DOCUMENTS 3,833,002 A    9/1974 Palma
4,655,771 A    4/1987 Wallstein
(Continued)

OTHER PUBLICATIONS

E1, Lamination, 2013, Wikipedia, http://en.wikipedia.org/wiki/lamination.*

(Continued)

*Primary Examiner* — Dah-Wei D Yuan
*Assistant Examiner* — Andrew Bowman
(74) *Attorney, Agent, or Firm* — Vidas, Arrett & Steinkraus, P.A.

(57) ABSTRACT

An endoprosthesis comprising a stent, a cover fully covering the stent wherein the cover has variable porosity in the radial direction; and an adhesion layer connecting the stent to the cover. Another aspect of the invention is a method of implanting an endoprosthesis which includes a stent, providing a cover with variable porosity in the radial direction, connecting the stent to the cover with an adhesion layer to form a covered stent, and implanting the covered stent within a body lumen of a patient.

18 Claims, 9 Drawing Sheets

(51) Int. Cl.
*A61L 31/14* (2006.01)
*B05D 1/00* (2006.01)
*A61F 2/90* (2013.01)

(56) References Cited

U.S. PATENT DOCUMENTS

| | | | |
|---|---|---|---|
| 4,705,516 A | 11/1987 | Barone et al. | |
| 4,850,999 A | 7/1989 | Planck | |
| 4,954,126 A | 9/1990 | Wallsten | |
| 5,026,377 A | 6/1991 | Burton et al. | |
| 5,061,275 A | 10/1991 | Wallstein et al. | |
| 5,201,757 A | 4/1993 | Hevn et al. | |
| 5,464,450 A * | 11/1995 | Buscemi et al. | 623/1.2 |
| 5,474,563 A | 12/1995 | Myler et al. | |
| 5,534,287 A | 7/1996 | Lukic | |
| 5,540,712 A | 7/1996 | Kleshinski et al. | |
| 5,575,818 A * | 11/1996 | Pinchuk | 623/1.15 |
| 5,630,840 A | 5/1997 | Mayer | |
| 5,645,559 A | 7/1997 | Hachtman et al. | |
| 5,693,085 A | 12/1997 | Buirge et al. | |
| 5,718,159 A | 2/1998 | Thompson | |
| 5,741,333 A | 4/1998 | Frid | |
| 5,755,774 A | 5/1998 | Pinchuk | |
| 5,797,949 A | 8/1998 | Parodi | |
| 5,824,049 A | 10/1998 | Ragheb et al. | |
| 5,888,201 A | 3/1999 | Stinson et al. | |
| 5,891,191 A | 4/1999 | Stinson | |
| 5,902,317 A | 5/1999 | Kleshinski et al. | |
| 5,957,974 A | 9/1999 | Thompson | |
| 5,957,975 A | 9/1999 | Lafont et al. | |
| 5,961,547 A | 10/1999 | Razavi | |
| 5,980,564 A | 11/1999 | Stinson | |
| 6,042,578 A | 3/2000 | Dinh et al. | |
| 6,156,064 A | 12/2000 | Chouinard | |
| 6,174,330 B1 | 1/2001 | Stinson | |
| 6,190,404 B1 | 2/2001 | Palmaz et al. | |
| 6,214,040 B1 | 4/2001 | Jayaraman | |
| 6,221,100 B1 | 4/2001 | Strecker | |
| 6,228,111 B1 | 5/2001 | Tomala et al. | |
| 6,245,103 B1 | 6/2001 | Stinson | |
| 6,254,632 B1 | 7/2001 | Wu et al. | |
| 6,261,320 B1 | 7/2001 | Tam et al. | |
| 6,290,722 B1 | 9/2001 | Wang | |
| 6,312,457 B1 | 11/2001 | DiMatteo | |
| 6,355,058 B1 | 3/2002 | Pacetti et al. | |
| 6,379,382 B1 | 4/2002 | Yang | |
| 6,383,214 B1 | 5/2002 | Banas et al. | |
| 6,398,802 B1 | 6/2002 | Yee | |
| 6,416,548 B2 | 7/2002 | Chinn et al. | |
| 6,436,132 B1 | 8/2002 | Patel et al. | |
| 6,451,050 B1 | 9/2002 | Rudakov et al. | |
| 6,506,437 B1 | 1/2003 | Harish et al. | |
| 6,514,283 B2 | 2/2003 | DiMatteo | |
| 6,626,939 B1 | 9/2003 | Burnside et al. | |
| 6,656,216 B1 | 12/2003 | Hossainy et al. | |
| 6,756,007 B2 | 6/2004 | Pletzer et al. | |
| 6,770,086 B1 | 8/2004 | Girton | |
| 6,827,737 B2 | 12/2004 | Hill et al. | |
| 7,060,087 B2 | 6/2006 | DiMatteo | |
| 7,736,687 B2 | 6/2010 | Sims et al. | |
| 7,955,374 B2 | 6/2011 | Erickson et al. | |
| 8,197,552 B2 | 6/2012 | Mandpe | |
| 8,435,285 B2 | 5/2013 | Shank et al. | |
| 2001/0039450 A1 | 11/2001 | Pavcnik et al. | |
| 2002/0010508 A1* | 1/2002 | Chobotov et al. | 623/1.44 |
| 2002/0058984 A1* | 5/2002 | Butaric et al. | 623/1.13 |
| 2002/0103527 A1 | 8/2002 | Kocur et al. | |
| 2002/0165601 A1 | 11/2002 | Clerc | |
| 2003/0045924 A1 | 3/2003 | Datta et al. | |
| 2003/0059463 A1* | 3/2003 | Lahtinen | 424/450 |
| 2003/0074049 A1 | 4/2003 | Hoganson et al. | |
| 2003/0114917 A1* | 6/2003 | Holloway et al. | 623/1.13 |
| 2004/0024448 A1* | 2/2004 | Chang et al. | 623/1.42 |
| 2004/0030377 A1* | 2/2004 | Dubson et al. | 623/1.13 |
| 2005/0049693 A1 | 3/2005 | Walker | |
| 2006/0195173 A1 | 8/2006 | DiMatteo | |

OTHER PUBLICATIONS

U.S. Appl. No. 08/640,253, filed Apr. 6, 1999, Stinson.
U.S. Appl. No. 08/993,985, filed Jan. 12, 2005, Burnside.
U.S. Appl. No. 08/946,906, filed Sep. 28, 1999, Thompson.

* cited by examiner

COMPOSITE STENT WITH INNER AND OUTER STENT ELEMENTS AND METHOD OF USING THE SAME

CROSS REFERENCE TO RELATED APPLICATIONS

This application is a continuation of U.S. patent application Ser. No. 10/962,567, filed Oct. 13, 2004 which is a continuation-in-part to "Composite Stent With Inner And Outer Stent Elements and Method Of Using The Same", U.S. patent application Ser. No. 10/720,176, by Peter Shank and F. Anthony Headley Jr., filed on Nov. 25, 2003.

BACKGROUND

Field of the Invention

The present invention relates to body implantable treatment devices, and more particularly to stents and other prostheses intended for fixation in body lumens.

Typically, a stent is delivered into position at a treatment site in a compressed state using a delivery device. After the stent is positioned at the treatment site, the delivery device is actuated to release the stent. Following release of the stent, self-expanding stents are allowed to self-expand within the body vessel or lumen. FIG. 1 shows such a configuration including a delivery device in the form of catheter 101 containing a portion 103 of self-expanding stent 102 within a lumen of the catheter having an outside diameter O.D. and an inside diameter I.D. Having exited an open distal end of the lumen, deployed portion 104 of stent 102 is shown expanding to a deployed diameter D.D. Alternatively, a balloon may be used to expand stents. This expansion of the stent in the body vessel helps to retain the stent in place and prevents or reduces movement or migration of the stent. FIG. 2 shows stent 201 being expanded within a body lumen 202. A Percutaneous Transluminal Angioplasty (PTA) or Transluminal Coronary Angioplasty (PTCA) balloon 203 is inflated to expand stent 201 and urge it into position against body lumen 202.

For stents that will remain in place, movement and migration may be reduced by leaving portions of the stent uncovered (typically the extreme upper and lower portions of the stent) so tissue can grow in to the stent to anchor it. Other approaches to reducing stent migration may include increasing the outside surface roughness or adding hooks to the outside of the stent. Removal can be difficult if tissue has grown into the stent, and if the stent is removed forcefully, tissue damage can occur.

Stents are typically composed of stent filaments, and may be categorized as permanent, removable or bioabsorbable. Permanent stents are retained in place and incorporated into the vessel wall. Removable stents are removed from the body vessel when the stent is no longer needed. A bioabsorbable stent may be composed of, or include bioresorbable material that is broken down by the body and absorbed or passed from the body after some period of time when it is no longer needed.

Commonly used materials for stent filaments include Elgiloy® and Phynox® metal spring alloys. Other metallic materials that may be used for stents filaments are 316 stainless steel, MP35N alloy and superelastic Nitinol nickel-titanium. Another stent, available from Schneider (USA) Inc. of Minneapolis, Minn., has a radiopaque clad composite structure such as shown in U.S. Pat. No. 5,630,840 to Mayer. Stents can also be made of a titanium alloy as described in U.S. Pat. No. 5,888,201.

Bioabsorbable implantable endoprostheses such as stents, stent-grafts, grafts, filters, occlusive devices, and valves may be made of poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(aminoacides), or related coploymers materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

Stents as described are used in the treatment of various medical conditions. One such condition, carcinomas in the esophagus may lead to progressive dysphagia, i.e. difficulty in swallowing, and the inability to swallow liquids in the most severe cases. While surgical removal of the carcinoma is sometimes effective, the majority of patients have tumors that cannot be surgically removed. Repeated dilations of the esophagus provide only temporary relief.

Difficult or refractory cases of carcinomas often are treated by intubation using rigid plastic prostheses, or laser therapy with an Nd:YAG laser. These techniques, while often effective, have disadvantages. Rigid plastic prostheses are large, for example having a diameter of 10-12 mm and larger (25-29 mm) outer end flanges. Placement of rigid plastic stents is traumatic, and too frequently causes perforation of the esophageal wall. These prostheses further are subject to migration, obstruction with food or tumor ingrowth, and damage to surrounding cells.

Laser therapy is expensive, typically requiring several treatment sessions. Tumor recurrence is frequent, in the range of 30-40 percent. Submucosal tumors, and certain pulmonary and breast tumors causing dysphagia by esophageal compression, cannot be treated by laser therapy.

Patients with benign tumors may also be treated with repeated dilatations using a balloon catheter or a bougie tube. Another treatment approach is submucosal resection. However, violation of the lumen wall carries the risk of wound contamination, as well as possible fistula formation. Following any treatment that alters the lumen wall, the lumen wall remains very sensitive during the healing process. The healing lumen wall can be repeatedly irritated by stomach contents refluxing into the esophagus or a passing food bolus. In addition, surgery is determined based on the absence of certain factors which significantly increase the risk of surgical mortality, morbidity, and long term adverse events. Factors such as cardiac risk, multisystem failure, general debility, malnutrition and infection limit the patient's health and chances of tolerating the radical curative surgical procedure. Thus, esophageal resection with reanastomosis is most appropriate only for very large tumors, annular tumors, or those densely adherent to larger areas of the lumen wall. Tumors at the anastomotic site often reocclude the esophagus and require the same treatments. Pulmonary resections have similar complications.

The search for a more suitable prosthesis has led to experiments with Gianturco stents, also known as Z-stents. U.S. Pat. No. 4,800,882 (Gianturco) describes such a device employed as an endovascular stent. Such stents for the esophagus have been constructed of 0.018 inch stainless steel wire, and provided with a silicone cover to inhibit tumor ingrowth. It was found necessary, however, to provide a distal silicone bumper to prevent trauma to the esophageal lumen wall.

Self-expanding mesh stents also have been considered for use as esophageal prostheses. U.S. Pat. No. 4,655,771 (Wallsten) discloses a mesh stent as a flexible tubular braided structure formed of helically wound thread elements. Mesh stents are unlikely to lead to pressure necrosis of the esophageal wall. With its inherent pliability the mesh stent, as compared to a rigid plastic stent, is insertable with much less trauma to the patient. Further, the stent can mold itself to, and firmly fix itself against, the esophageal wall to resist migration.

Thus, both malignant and benign strictures of the esophagus and pulmonary tree may be treated using self-expanding metal stents (SEMS). SEMS allow patients to return to a more normal diet thereby enhancing their quality of life. Generally, benign strictures are treated with SEMS only as a last resort. However, a major complication in both malignant and benign cases is stent/lumen re-occlusion over time. That is, the stent is subject to tumor ingrowth because of the spaces between adjacent filaments. This is due, at least in part, to the need to combine sufficient radial force with some open stent mesh to allow tissue incorporation so as to anchor the stent in place. As tissue grows through the mesh (in-growth), and around the stent ends (overgrowth), the body lumen often becomes re-occluded over time. This makes separation of the stent or a stent cover from surrounding tissue difficult. Irritation and inflammation of tissue can result from an anchored stent or its cover being removed. Therefore, there is a need for a covered stent that can establish anchoring quickly, yet can be easily removed when required.

Stents may also be covered with various materials to encourage or inhibit tissue attachment to the stent. Covered stents are gaining favor for biliary applications because they more effectively inhibit tissue attachment, intrusion, and constriction of the tract than bare stents. For example, polytetrafluoroethylene (PTFE) covered stents are desirable for removable stents because tissue attachment or in-growth is reduced in comparison to bare stent or a stent covered with textile (polyester) material. Laminated ePTFE may also be used to cover stents. U.S. Pat. No. 5,843,089 of Sahatjiian et al. describes a stent coated on its inner surfaces with hydrogel (i) to protect cells of the lumen which may have been damaged during deployment of the stent, (ii) to reduce flow disturbances, and (iii) for the delivery of therapeutic agents embodied in the gel.

As stents are covered with material to aid in their removal, stent migration from the treatment site increases. There remains a continuing need for covered stents which include characteristics to maintain the stent in position at the treatment site. For example, stents covered with ePTFE, such as Precedent, are easily removed after a given time period, such as six months, but may not provide sufficient fixation to prevent the risk of migration during the six month period. U.S. Patent Application Publication No. US 2002/0177904 describes a removable stent having a bioabsorbable or biodegradable polymeric outer coating that maintains a helical configuration of the stent for some period of time. Upon degradation or absorption of the coating, the stent is converted back into a soft, elongated shape. U.S. Patent Application Publication No. US 2002/0002399 describes another removable stent structure including an outer bioabsorbable/degradable coating providing rigidity for some period of time after which the stent reverts to a softened filament for removal. U.S. Pat. No. 5,961,547 describes a similar temporary stent structure.

SUMMARY OF THE INVENTION

An endoprosthesis comprising a stent, a cover fully covering said stent wherein said cover has variable porosity in the radial direction, and an adhesion layer connecting said stent to said cover. Another aspect of the invention is a method of implanting an endoprosthesis which includes providing a stent, providing a cover with variable porosity in the radial direction, connecting said stent to said cover with an adhesion layer to form a covered stent, and implanting said covered stent within a body lumen of a patient. Yet another aspect of the present invention is an apparatus comprising covering means with variable porosity in the radial direction, means for providing radial, outwardly directed force to said covering means, and means for connecting temporarily said covering means to said means for providing radial, outwardly directed force. Still another aspect of the present invention is the process for making a covered stent comprising the steps of mounting a stent on a mandrel, applying an adhesion layer onto the external surface of said stent while spinning said mandrel, and applying a stent cover of variable porosity onto said adhesion layer.

BRIEF DESCRIPTION OF THE DRAWINGS

We first briefly described the drawings.

DETAILED DESCRIPTION

Figure 3:
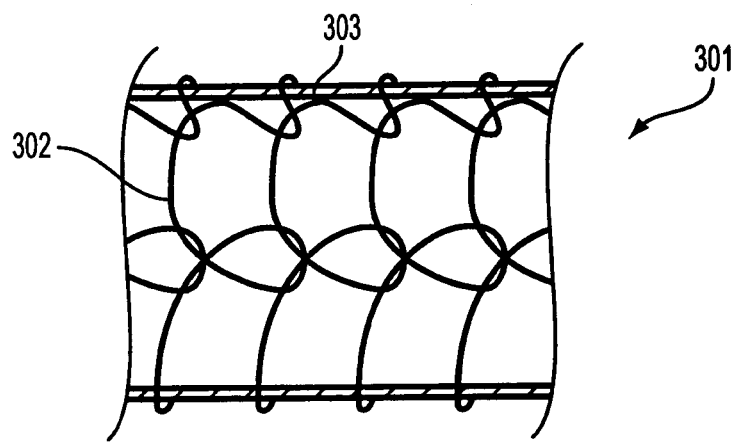
FIG. 3 is a diagram of an embodiment of the present invention including an inner self-expanding metal stent (SEMS) element located within an outer knitted bioabsorbable stent element, both of which are in a compressed state.
Figure 4:
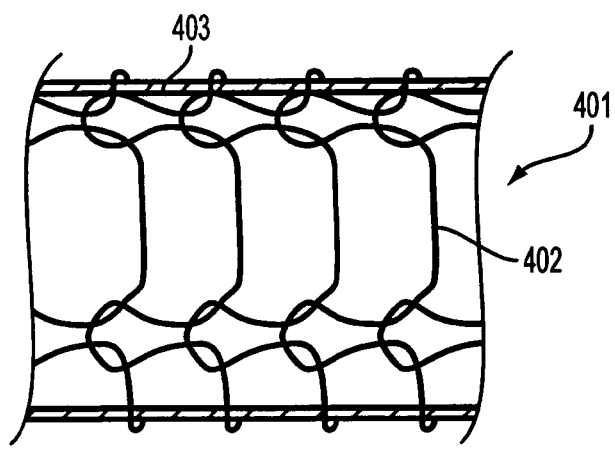
FIG. 4 is a diagram of the inner SEMS element and outer knitted bioabsorbable stent element embodiment of FIG. 3 in an expanded state such as in position in a body lumen.

Referring to FIG. 3, according to an embodiment of the invention, a composite stent 301 includes an outer bioabsorbable mesh or similar stent element 302 affixed to a fully covered inner self-expanding metal stent (SEMS) 303 (only the covering of inner stent in visible). Suitable outer bioabsorbable or biodegradable stents are typically made from a bioabsorbable polymer. Polymer structures typically have a higher potential to creep (i.e., experience permanent deformation and fail to return to an original shape and/or size when released) if held in a constrained condition while in the delivery system. The potential for creep in the outer element may increase with temperature elevation such as in sterilization. The fully covered SEMS 401 will self-expand as shown in FIG. 4 so that the combined structure 401 (covered inner SEMS 403 and bioabsorbable mesh 402) overcomes any loss in recovered diameter. Only the covering of the inner stent is shown in FIG. 4. While some bioabsorbable shape memory polymers may minimize creep, the instant composite stent design simplifies the bioabsorbable material demands. Another advantage of the present invention is that the outer element is not required to support the lumen walls by itself. The inner element may assist the outer element in this respect. Therefore, the outer element may have a lower profile, such as a smaller diameter filament or a flat filament. Through the interaction of the inner element and the outer element the final body lumen diameter, with the stent in place, will have a larger diameter.

This general composite structure provides several advantages. For example, a radiopaque (RO) substance is often added to a stent to assist in identifying the position of the stent within the body lumen. Without the inner covered SEMS, the bioabsorbable component of the stent would need to be loaded with a RO substance to enable fluoroscopic visualization upon deployment. Unfortunately, addition of RO substances to the polymer weakens the polymer thereby limiting the radial strength of the device, and leaving behind a potentially undesirable residual substance when the bioabsorbable element degrades. However, in various embodiments of the present invention, a composite stent may be configured to place the radiopacity into the inner element or a covering of the inner element. This may be done by making an element of the stent of a RO material, placing markers within the element or the covers, incorporating a RO core within an element or by similar methods.

Once the composite stent structure is in place, the bioabsorbable outer stent will, over time, become incorporated into the lumen wall which will keep the combined structure from migrating. The outer element of the present invention may also provide interference or friction to prevent migration prior to integration into the lumen wall. Other methods of preventing migration included within the present invention include hooks or anchors on either stent or cover, adhesives to attach to the vessel wall, designing the outer stents with bumps or ridges or a unique cross-section, suturing or fastening the stent in place in the body, flaring the ends, or having retainer rings of larger diameter included at the end of the stents and similar methods and devices.

Addressing the inner element, while any stent element may be used for the inner element, Nitinol SEMS are known to have sufficient radial force and apply a gradual pressure against the force of the stricture and lumen wall. The bioabsorbable/removable SEMS structure retains the gradual pressure advantage of SEMS that may be compromised with a bioabsorbable stent alone. To obtain a radial force like that of SEMS, a much thicker filament would otherwise be required. The present composite stent technology minimizes the formation of scar tissue and allows for the use of more flexible bioabsorbable structures with smaller diameter bioabsorbable filaments. An inner stent cover may be included to provide a barrier to incorporation of the inner stent which enables its eventual removal. According to one embodiment, a fully covered inner section may be removed immediately (within the first day), acutely (within 1-21 days), or chronically (greater than 21 days) following placement of the outer member. The bioabsorbable element or the inner element may be used to fully deploy the outer element, thus avoiding the use of a balloon or other mechanical dilator. In addition to assisting in positioning the outer element, a fully covered SEMS shields the healing lumen wall from recurrent injury associated with stomach acid reflux, food, fluids or other substances that travel through the lumen. This in turn may reduce the amount of scar tissue formed on the lumen wall. Further, tissue buildup is limited to the bioabsorbable filament thickness which defines the gap between the lumen wall and cover.

The combined structure of the composite stent enables removal of the inner element to leave behind only the temporary-absorbable element. The two may be attached by a non-degrading ("permanent") or bioabsorbable means such as sutures, clips, staples, dissolvable gel, adhesive or mechanical interlock. Connectors incorporating easily removable means may also be used, such as interwoven filaments which may be pulled out, a crochet that may be unraveled or an inner element which may be "unscrewed" from an outer element. The connection may be made at the extremes of the stents (i.e. through the last row of loops or cells) or anywhere along the length of the structure. The two may be separated by mechanical means such as a snare, scissors, forceps, laser or a combination of these to sever the connecting component. Alternately, they can be separated through absorption if a bioabsorbable connector is used such as a dissolvable adhesive or a pH-reactive connector.

When certain material is chosen, the bioabsorbable backbone, typically the outer element, will become fully incorporated into the lumen wall within approximately four weeks. Typically, once the bioabsorbable stent elements are incorporated, scar tissue will be formed that surrounds and eventually replaces the stent to support the lumen. To accomplish this the bioabsorbable-polymer stent must be in intimate contact with the lumen wall to allow for incorporation. If the stent does not fully expand against the lumen wall or cannot resist the external load from the stricture during healing, the lumen will become occluded and dysphagia will return. The inner element such as the SEMS pushes and keeps the bioabsorbable backbone in contact with the lumen wall to promote healing without requiring the bioabsorbable structure to take the full load or gradually expand the lumen. Alternatively, the inner element may be balloon expandable. After the incorporation time period, once the site has fully healed, the fully covered inner SEMS may be removed.

The outer bioabsorbable element may be in a form other than a stent mesh. A graft, tube, stent or similar structure may be attached to the inner element to enhance the function of the combined structure. Likewise, the inner element may be in a form other than a stent mesh. In one embodiment, any expandable structure may be used to self-expand the combined structure. Examples may be, but are not limited to, a dilator, vena cava filters, venous valves, gastro esophageal valves, etc.

The inner element may be made bioabsorbable or degradable and the outer element may be made from a non-absorbable material in some embodiments. This may be desirable where, for example, a permanent implant provided by the outer element lacks the necessary integrity by itself to resist loading prior to incorporation and/or where a secondary procedure to remove the implant is not possible or desirable. In these embodiments, the outer element remains as a permanent implant after all or a portion of the inner element has been bioabsorbed or degraded. Such a bioabsorbable inner backbone may include elements that are non-absorbable and designed to continue to function after removal of the inner element and/or after the bioabsorbable element has degraded. Examples of this may be mechanisms such as valves for anti-reflux control of stomach contents back into the esophagus, mechanisms such as valves to control reflux of blood from the arterial to venous vessels in the circulatory system (i.e., arterial-venous fistulas in the arm or legs), and mechanisms such as valves for the venous system to address DVT. Similarly, use of the outer covering on the inner element will facilitate the same protection of the healing tissue with an alternate outer structure.

In some embodiments the composite stent structure may also be used as a means for agent delivery. The outer bioabsorbable element, the inner element or the filament material used for either may be impregnated or coated with an agent in a coating or gel form. This may include outer or inner elements with agents and means of deploying those agents. Such means include, but are not limited to: agent directly on the device, agent within coating of the device (coating being either eluting or responding to triggers such as pressure, sponge, or body heat), device with channels, reservoirs, pores or means to hold agents, the agent within degradable structures such as the device itself or the coating on the device, agents applied by other devices such as delivery catheters or balloons, devices with reservoirs wrapped around, agents within the attachment means, or agents released by deployment of either device such as by cracking open the sheath. Further, various coatings may be used to improve the radiopacity, alter the lubricity and/or the surface texture, or as means to form the cover in the internal SEMS element. All of these offer means to improve the function, imaging, therapeutic value, and/or manufacturability of the device. A preferred embodiment for agent delivery is a coated outer stent.

According to another embodiment of the invention, the form of the outer element may be modified to assist in the application of agents. These alternate forms of the outer element may be made to contact or penetrate the lumen wall. Accordingly the outer element may be made blunt or sharpened depending upon the desired intent. Additionally, the form of the outer element may assist in stabilizing the composite stent in place, or increase its therapeutic value by delivering a great quantity of agent.

Attachment of the inner and outer element may be accomplished using various means, structures and techniques. For example, the inner and outer elements may be attached during manufacturing or deployed separately and attached in-vivo. Various attachment means may also be used. For example, as will be further described, the two may be mechanically interlocked by mechanical means such as screwing together or alignment of a boss and slot.

The present invention provides several benefits. For example, plastic stents, whether bioabsorbable or of another non-bioabsorbable polymer, usually do not have the radial force of the expanding metal stents (SEMS) such as Ultraflex™ or Wallstent®. The present invention may be used to assist in fully expanding these stents to their intended final diameters once positioned at the site of the stricture.

Further, plastic stents, whether made of a bioabsorbable or non-bioabsorbable material are subject to creep under a sustained load. These stents are often loaded or compressed while preloaded on the delivery system (with or without elevated temperature and humidity associated with sterilization and/or handling). If the stent is held in a constrained configuration where the initial stent diameter is reduced significantly to allow placement into the body, the plastic will likely permanently deform or creep under the load. If a stent has taken a permanent set or deformity due to packaging and delivery, the size and shape of the stent upon placement into the body of the patient may be incorrect and result in creep after placement. The present invention may be used to eliminate or reduce this creep.

Figure 5:
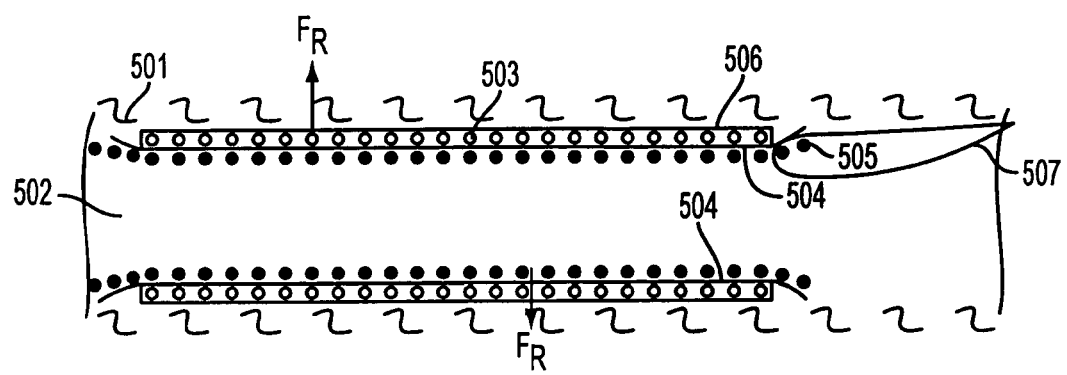
FIG. 5 is a cross-sectional view of an embodiment of the present invention including an outer bioabsorbable element positioned within a removable inner element in situ including retrieval loops for removal of the inner element.

To address the condition where the material creeps due to the load applied during prolonged constrainment on the delivery system and/or due to the sustained and potentially increasing load from the tumor or stricture, the bioabsorbable stent can be affixed to a removable stent. According to one embodiment of the invention as shown in FIG. 5, composite stent 502 includes a polymeric outer element 503 which is detachably mounted onto a SEMS inner element 505 forming an inner covering over outer element 503. The inner SEMS element applies a sustained outward radial force FR on a stricture in the lumen or tumor present in the surrounding lumen wall 501 to maintain or eventually achieve the desired body lumen diameter. The SEMS is selected to have a radial force FR sufficient to push the stricture outward to open the lumen or vessel.

SEMS used as inner element 505 may be left in place for a period of time to allow the polymeric outer stent element 503 to become incorporated into body lumen wall 501. The typical time range for incorporation of a stent into a vessel or lumen wall is one to three weeks, but may vary depending upon a number of parameters, including materials, geometry, tissue type and condition and force on the tissue.

SEMS inner element 505 may include covering 504 over the length upon which the polymeric stent outer element 503 is held. The covering formed over inner element 505 functions to block the tissue from incorporating into the removable SEMS and confine the ingrowth to the bioabsorbable outer element 503. With tissue incorporation around the polymeric stent (outer element 503) and not into the SEMS (inner element 505), the SEMS may be more easily removed with less tissue damage. FIG. 5 also illustrates one location of retrieval loop 507, which may be used to remove inner element 505.

Figure 1:
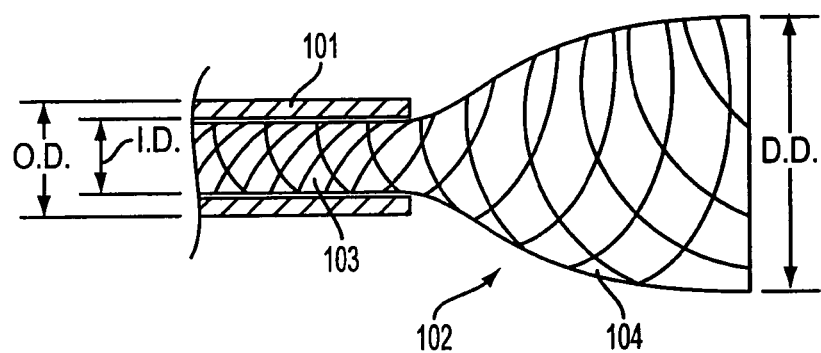
FIG. 1 is a diagram of a stent delivery system including a partially deployed stent.
Figure 2:
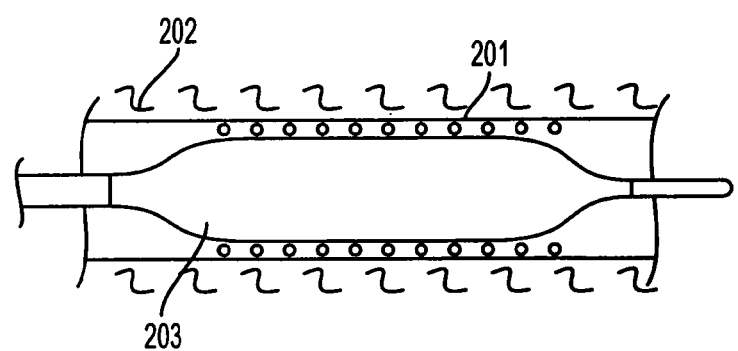
FIG. 2 is a diagram of a Percutaneous Transluminal Angioplasty (PTA) or Transluminal Coronary Angioplasty (PTCA) balloon being used to expand a stent within a body lumen.

The SEMS may serve multiple purposes. Upon deployment, the SEMS carries the outer stent element with it through its self expansion and helps to deploy the outer stent element. This avoids the need for using a balloon catheter to deploy the outer stent element as shown in and described in FIG. 2. Further, the SEMS maintains a radial force against the stricture or lesion. Should the outer stent element not be able to exert force against the stricture the SEMS could compensate for this by providing additional outward radial force.

The SEMS may be removed after the outer stent element has been incorporated into the wall. This removal may be accomplished through use of retrieval loop 507. Once incorporation has occurred, the vessel will be less likely to reduce in size as scar tissue creates a scaffold limiting the lumen or vessel to the desired size.

The outer stent element may be held to the SEMS using a dissolvable gel that adheres the outer stent element to the covered SEMS, or by bioabsorbable or biodegradable sutures, clips, or staples, or by an adhesive that has a low break away strength. Additionally, biodegradable adhesives, bosses, and triggerable dissolution connections may be used to connect the inner and outer elements. Electrical, thermal, light energy, chemical activation and other triggering methods may be used.

In another embodiment of the present invention, either the inner stent element or the outer stent element may include radiopaque characteristics. Radiopacity may be provided in some embodiments by including radiopaque fillers. Radiopaque fillers include compounds such as barium that may be mixed integrally or coated on the stent materials. In some situations, fillers may not function optimally; they may compromise the physical characteristics and performance of a device or may be undesirably released into the body. Preferably, the radiopacity of the device is provided by virtue of innate material properties. In one such embodiment, the SEMS inner stent element may provide sufficient radiopacity to the otherwise radiolucent polymeric outer stent element. In further embodiments, radiopacity may be imparted to the composite stent device by addition of radiopaque filaments or structures within the radiolucent outer stent element. In some embodiments, one or more radiopaque markers are added to either of the stent elements. An alternative to fillers may include a tracer filament or stent within the bioabsorbable or polymeric stent. This is done by using a metallic wire or marker attached or incorporated into the stricture. This of course results in this material being incorporated into the lumen wall or endothelium.

A further advantage of the retrievable SEMS with a bioabsorbable element system includes the ability to deliver and localize therapeutic agents (agents) or other, e.g., radioactive seeds.

Figure 6:
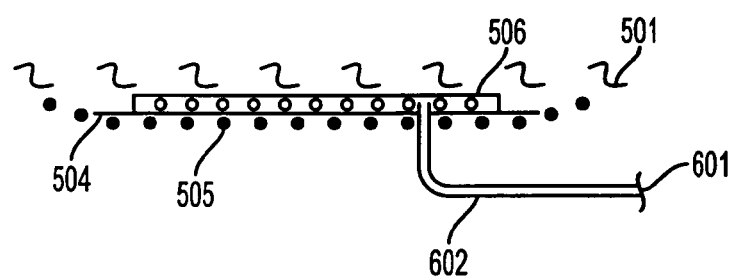
FIG. 6 is a partial cross-sectional view of an embodiment of the present invention which includes an inner and outer stent elements in situ, the outer element including means for accepting in situ application and/or replenishment of a therapeutic agent.

The bioabsorbable stent and/o SEMS cover may be impregnated, compounded or coated with an agent to enable a very localized delivery of agents to the lumen wall or vascular wall. The SEMS applies a radial force to keep the bioabsorbable stent element in contact with the surrounding lumen wall to allow agent or therapeutic agent uptake. The force may also be used to push the therapeutic agent into the surrounding lumen wall. Additionally, if configured as a retrievable stent, the SEMS may be removed when the therapeutic agent has been delivered or replaced with another stent element comprising a therapeutic agent to effect another cycle of administration. Further, the covered SEMS, if covered with a outer stent element that has been doped, impregnated, compounded, or coated with a therapeutic agent, would shield the outer element from bodily fluids that might otherwise displace the therapeutic agent. Thus, as shown in FIG. 6, using a bioabsorbable or polymeric structure on the back of the SEMS provides an integrated agent delivery-reservoir system. As shown therein, a cover 504 may include dissolvable gel 506 into which a therapeutic agent 601 may be injected through line 602. Therapeutic agent 601 is then forced into the surrounding lumen wall or endothelium 501 by the radial force expressed by inner removable stent 505.

Thus, according to this configuration, a reservoir is formed into which therapeutic agents may be loaded. The agents may be delivered to recharge the reservoir via an injection by needle or catheter or by use of an agent delivery balloon attached to a catheter. In a further embodiment, it is possible to replace the inner stent element with another inner stent element comprising a therapeutic agent as illustrated in FIG. 5.

Covering 504 on the SEMS of FIG. 6 may be used to create a barrier to hold a therapeutic agent and isolate the body lumen from passing bodily fluids (e.g. stomach acid) or gases. Covering 504 may extend the length of the element or a portion thereof. The outer stent element, if formed with a mesh consistency (woven, braided, knitted or other) may hold the therapeutic agent with the wall of the outer stent element or between the inner stent element and the outer stent element. According to an alternative embodiment, as the bioabsorbable element on the body of the SEMS dissolves, the resulting space remaining may be replaced or filled with the therapeutic agent. This allows the body lumen wall to be treated further with the therapeutic agent, even in situations where scar tissue may have formed around the outer stent element.

Figure 7:
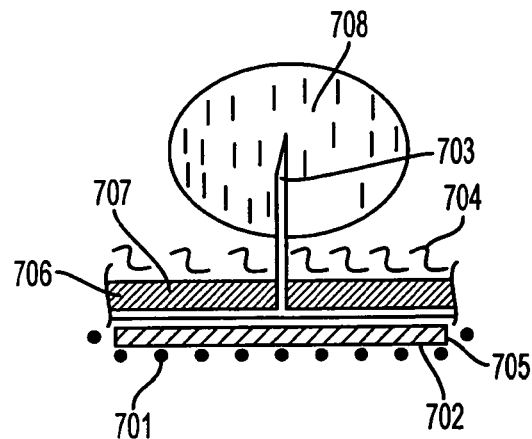
FIG. 7 is a diagram of an embodiment of the present invention of a composite stent which includes an integral reservoir of a therapeutic agent fluid and a bioabsorbable needle delivery system.

In alternate embodiments, as shown in FIG. 7, retrievable SEMS 702 includes inner stent element 701 and covering 705. This configuration enhances the administration of agents to the body lumen wall 704. In some embodiments, bioabsorbable element 703 is a needle. In alternate embodiments, element 703 is a protrusion into the body lumen wall or fibers capable of drawing agent 707, stored in reservoir 706 towards the lumen wall 704. For example, as shown in FIG. 7, bioabsorbable needle 703 may be configured to "wick up" a therapeutic agent 707 stored in the form of a fluid in reservoir 706, injecting agent 707 into tumor 708. This may occur through lumen wall 704.

The inner stent element may also be equipped with a bioabsorbable filament which gives a physician access, through the lumen wall, into tissue below the surface. This access may give the physician a conduit to the underlying tissue (or tumor) as the polymer breaks down. In one embodiment, as the polymer breaks down, it may be replaced with the therapeutic agent. In this embodiment, the positive force from the inner stent element would push the therapeutic agent to the intended site. A reservoir to hold the therapeutic agent may be formed of a bioabsorbable or pressure sensitive weeping-type membrane sack to allow the therapeutic agent to ooze out of the reservoir. In this and other configurations, a needle could serve to wick a therapeutic agent. Alternatively, the body of a needle may comprise a therapeutic agent which is delivered as the needle degrades.

Figure 8:
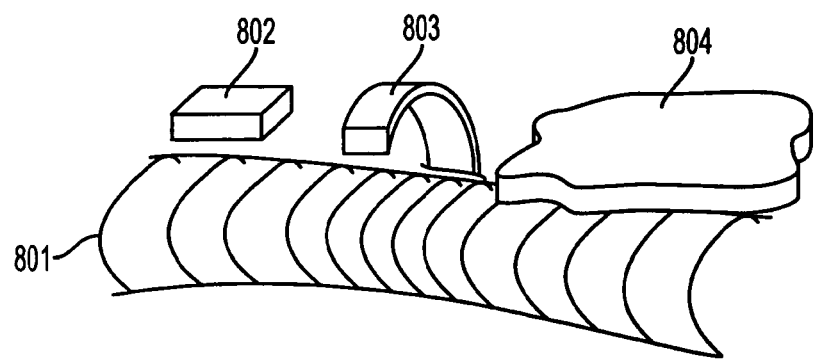
FIG. 8 is a diagram depicting alternate outer stent element configurations.

FIG. 8 illustrates alternative biodegradable structures that may be positioned at a treatment site and held in place by SEMS 801 until incorporated into the surrounding tissue. In addition to a sack-like reservoir or a weeping reservoir 804, therapeutic agents may be delivered to the body lumen wall by use of agent delivery devices located external to the outer stent element. Such devices include, but are not limited to, a film or other wrapping, one or more bands 803 extending substantially around the circumference of the outer stent element or one or more clips 802 which may deliver a localized amount of agent depending upon the position on the outer stent element.

Figure 9:
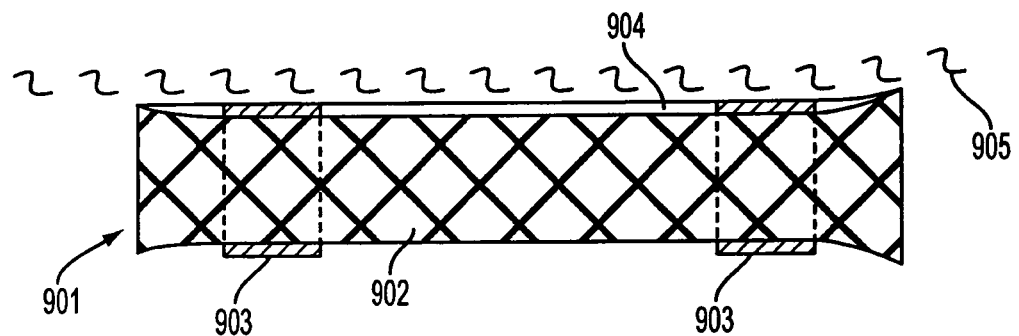
FIG. 9 is a sectional view of an embodiment of the present invention of a composite stent which includes incorporating a fluid reservoir held in place in a body lumen by axial bands of tissue adhesive.

FIG. 9 illustrates another embodiment 901 in which a reservoir for holding a therapeutic agent is formed by a cavity created between the stent and the body lumen wall using a covered SEMS. Cover 904 of element 902 may form a reservoir impregnated with or covered with an agent. The contact with body lumen wall 905 may enable transfer while the cover itself would shield the environment. Additionally, the cover 904 may comprise a hollow membrane filled with an agent and possibly an agent carrier, a sponge-like material, a hydrogel polymer or similar items. Tissue adhesive 903 may also be included on both ends of the element.

Figure 10:
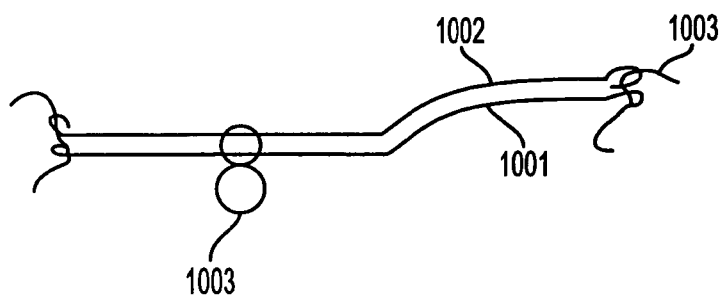
FIG. 10 is a diagram of an embodiment of the present invention which includes a bioabsorbable outer stent attached to an inner element by sutures.
Figure 11:
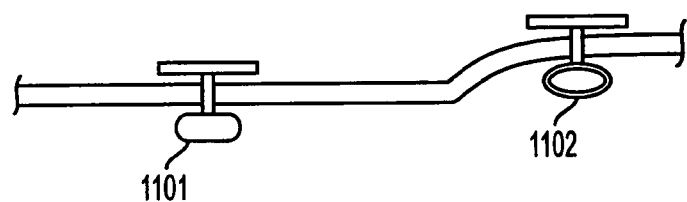
FIG. 11 is a diagram of an embodiment of the present invention which includes a bioabsorbable outer stent attached to an inner element by tabs or clips.
Figure 12:
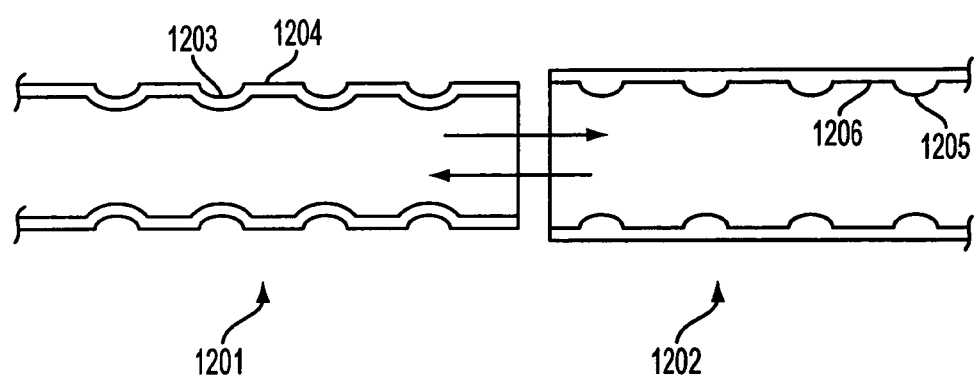
FIG. 12 is a cross-sectional view of an embodiment of the present invention which includes mating surfaces of inner and outer elements having a threaded configuration for retaining one inside the other.

FIG. 10 depicts another embodiment in which the bioabsorbable outer stent element 1002 is connected to inner element 1001 using a bioabsorbable or non-bioabsorbable suture 1003 at the extreme ends of the stent or at any point within the length of the two elements. Alternatively, a third intermediate layer may be positioned between the outer stent element and the inner stent element to cause the stent elements to remain intact. This intermediate layer may include grooves, lands or other features to maintain contact between the stent elements. Additionally, the inner and outer element may be interwoven at specific points, preferably with a degradable filament which would allow the elements to be separated at a later time. In one embodiment, one or more sutures may be used to connect the outer stent element to the inner stent element. Using scissors or cutting tool, the suture may be severed and pulled out. Alternatively, sutures 1003 illustrated in FIG. 10 may be replaced with tabs 1101 or clips 1102 to connect the two elements as shown in FIG. 11. According to other embodiments of the invention, the inner and outer elements may be mechanically interlocked using still other means as shown in FIG. 12. Inner stent element 1201 may include a configuration of grooves 1203 and lands 1204 configured to mate with respective lands 1205 and grooves 1206 of outer biodegradable element 1202. Likewise, the two elements may be mated together by a dovetail-like connection (not shown), or the two may be screwed together wherein locking structures, such as helical grooves or threads, are formed on mating surfaces of the elements. By utilizing the inner covered element to limit tissue incorporation around the element the two elements may be easily unscrewed or disconnected even after an extended period.

Figure 13:
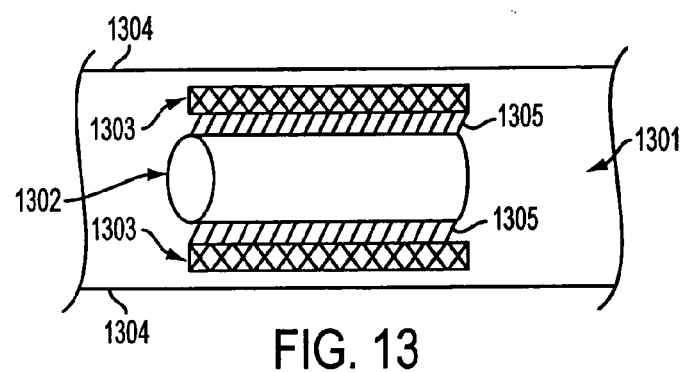
FIG. 13 shows an endoprosthesis according to an embodiment of the present invention.

In FIG. 13, an endoprosthesis 1301 is shown. The endoprosthesis 1301 includes a stent 1302 that may be generally cylindrically in shape. Stent 1302 may be constructed of a variety of materials using a number of different construction methods. Additionally, stent 1302 may be a self-expandable stent, or may be expanded using a balloon catheter or other methods. Stent 1302 may be of various designs including, for example, mesh and helical braided stents. Generally, stent 1302 may be composed of metals such as nitinol or stainless steel, plastic, ceramic, polymers, composite materials, tantalum, cobalt, or titanium-cobalt alloy. More specifically, stent 1302 may be constructed of a biopolymer such as Dacron, PTFE silicon, Fibrin AAA, collagen, poly(alpha-hydroxy acid) such as poly-L-lactide (PLLA), poly-D-lactide (PDLA), polyglycolide (PGA), polydioxanone, polycaprolactone (PCL), polygluconate, polylactic acid-polyethylene oxide copolymers, modified cellulose, collagen, poly(hydroxybutyrate), polyanhydride, polyphosphoester, or poly (aminoacides). Stent 1302 may be absorbable or dissolvable, or may be non-absorbable. Stent 1302 may also be removable, including both temporary and retrievable-type stents, in some embodiments. Stent 1302 is covered on the surface nearest the body lumen 1304 by stent cover 1303 which is located between stent 1302 and the body lumen 1304. In a preferred embodiment, stent 1302 is fully covered by stent cover 1303 such that no surface feature of stent 1302 may directly contact body lumen 1304 without interposed stent cover 1303 in place. Stent cover 1303 may be connected to stent 1302 by adhesion layer 1305, located between stent cover 1303 and stent 1302.

Stent cover 1303 may have variable porosity in the radial direction in a preferred embodiment. For example, the outer wall of stent cover 1303 that contacts body lumen wall 1304 may have high porosity to promote tissue in-growth and adhesion of stent cover 1303 to body lumen wall 1304. In contrast, the inner wall of stent cover 1303 in this example may be of very low porosity or may even be a solid film to reduce cell or fluid transfer. Other porosity combinations may be used to design covered stents with desired adhesion and removal characteristics. Various materials may be used to form stent cover 1303, such as polyurethane, block copolymers, Dacrone, PTFE silicon, ethylene vinyl acetate (EVA), silicone rubber, ethylene propylene copolymer, styrene, ethylene, or butylene styrene block copolymer. While non-biodegradable materials may be used in a preferred embodiment, a stent cover 1303 may also be made of biodegradable materials. Stent cover 1303 may be formed of several layers of different materials such that a stent cover 1303 of variable porosity is formed. Stent cover 1303 materials may be shaped to form an interlocking mesh with specific pore size.

Adhesion layer 1305 may incorporate a number of materials and designs to keep stent cover 1303 and stent 1302 connected. Generally, adhesion layer 1305 may be made using a non-degradable or non-bioabsorbable material. Non-degradable or non-bioabsorbable materials may include metals, plastics, or other solids and may be in the form of fasteners such as clips or sutures. Non-degradable or non-bioabsorbable materials may be used in adhesion layer 1305 in combination with biodegradable or dissolvable materials. In a preferred embodiment, adhesion layer 1305 may be a biodegradable or dissolvable material. Biopolymers such as collagen, Alignate, Fibrin, PLA, PGA, PLA/GA copolymer, and PCL may be used. In some embodiments, the degradation of adhesion layer 1305 may be triggered at a selected time. Triggering may be accomplished by applying a triggering agent such as energy in such forms as heat, radiofrequency energy, laser radiation, x-ray and gamma ray radiation, or particle energy such as electron, neutron, or alpha particle radiation. The use of electricity or magnetic fields as triggering agents may be used to trigger adhesion layer 1305 degradation. Chemical triggering agents may also be used in some embodiments, where adhesion layer 1305 is treated with a compound that causes degradation of adhesion layer 1305. Treatment of adhesion layer 1305 with a triggering agent may occur after endoprosthesis 1301 is in place in a body lumen, or may occur before endoprosthesis 1301 is inserted in a body lumen. Alternatively, adhesion layer 1305 may be removed using mechanical force, or may be removed using any combination of the above mentioned separation means, for example, using heat and solvent, et cetera for removal. In addition combinations of the above mentioned separation means, or other known separation means may be used to separate the elements. Removal or degradation of adhesion layer 1305 results in the stent 1302 and stent cover 1303 remaining in place in the absence of external force. In a preferred embodiment, application of external force applied to stent 1302 will result in the stent cover 1303 remaining in place while the stent 1302 is removed from the body. For example, the stent 1302 may be made to stretch longitudinally, causing its diameter to become smaller and detaching from the stent cover 1303. In a preferred embodiment, stent cover 1303 may remain attached to the body lumen wall 1304 after the removal of stent 1302. In one example, an esophageal stent with cover may be placed in the esophagus. The stent is left in place until tissue ingrowth begins to anchor the cover, at which time it may be removed. In this example, an adhesion layer may be used to bind the stent with its cover, and the adhesion layer may be degradable. The stent and cover in this example reduce trauma to the patient and avoid irritation to the body lumen wall by eliminating any forceful separation of the device and any ingrown tissue. Adhesion layer 1305, stent cover 1303, or stent 1302 may also incorporate radiopaque materials to aid in locating an endoprosthesis 1301 within a body lumen 1304.

Figure 14:
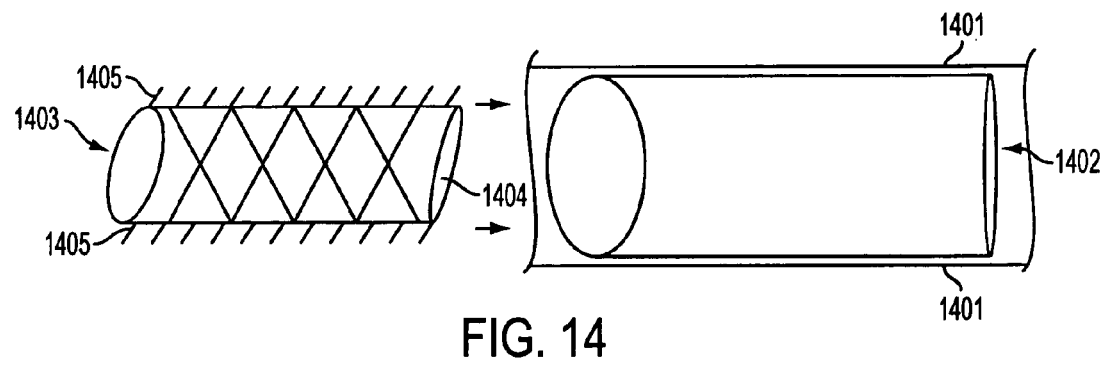
FIG. 14 shows a method of inserting a covered stent into a body lumen.

FIG. 14 shows a method of inserting a covered stent into a body lumen. Stent cover 1402 is inserted into body lumen 1401 using a delivery device. Following insertion of stent cover 1402, stent 1403 is inserted into stent cover 1402 such that stent cover 1402 completely covers stent 1403. Stent 1403 is composed of an inner stent layer 1404 that is covered by adhesion layer 1405. Adhesion layer 1405 binds stent 1403 to stent cover 1402 until such time as adhesion layer 1405 degrades. Stent 1403 may then be removed from stent cover 1402 by the application of external force. Stent 1403 may also comprise a biodegradable or dissolvable material such that removal of stent 1403 by external force is not necessary and degraded stent materials will pass harmlessly from the body lumen 1401. Adhesion layer 1405 degradation may be triggered at a selected time in some embodiments of the present invention. In other embodiments, stent cover 1402 may be bound to stent 1403 by adhesion layer 1405 before insertion into a body lumen. Of course, any of the above mentioned connection means may be utilized, such as, for example, fasteners.

Figure 15:
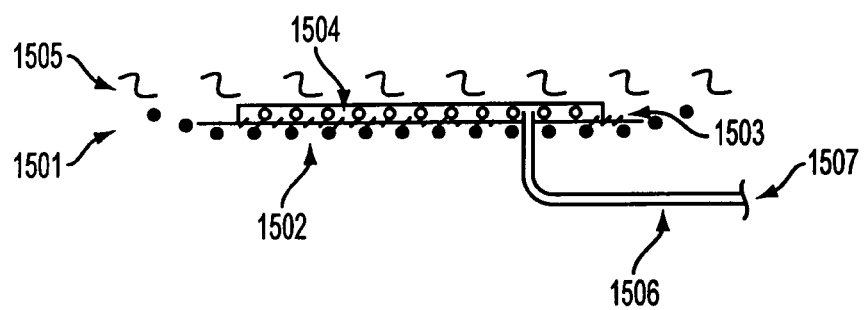
FIG. 15 shows a method of treatment of a stent cover with a bioactive agent.

FIG. 15 shows a method of treatment of a stent cover with a bioactive agent. Endoprosthesis 1501 may be placed in a body lumen 1505. Endoprosthesis 1501 may comprise a stent 1502 located radially inward of an adhesion layer 1503 that connects the stent 1502 to a stent cover 1504. Stent cover 1504 is in physical contact with the inner wall of a body lumen 1505 in a preferred embodiment. Stent cover 1504 may be treated with a bioactive agent 1507 that is injected into stent cover 1504 through a line 1506. Examples of bioactive agents used in this embodiment may include, but are not limited to, various drugs and chemical compounds such as taxol, carboplatin, interleukin, steroids, et cetera, radioisotopes and other materials used in nuclear medical disease management, anesthetics, and other treatment modalities.

Figure 16:
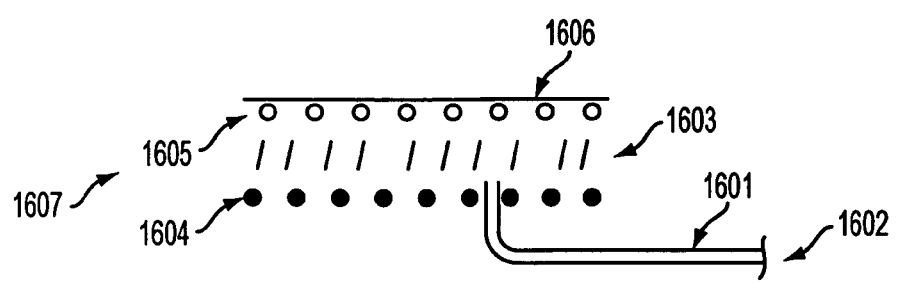
FIG. 16 shows an alternative embodiment of the present invention, where an endoprosthesis in a body lumen may be treated with a triggering agent.

FIG. 16 shows an alternative embodiment of the present invention, where an endoprosthesis in a body lumen may be treated with a triggering agent. Line 1601 may be used to deliver a triggering agent 1602 to an adhesion layer 1603. Triggering agent 1602 may cause adhesion layer 1603 to degrade, thus eliminating a connection between stent 1604 and stent cover 1605. Stent 1604 may then be removed by application of external force from a removal device, or may degrade. In other embodiments, triggering agent 1602 may cause the degradation of stent cover 1606 and/or stent 1605.

Figure 17:
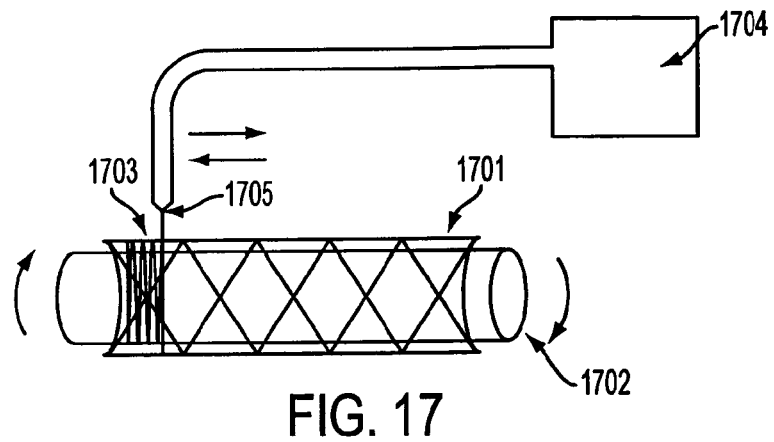
FIG. 17 shows a process for manufacturing a covered stent according to an embodiment of the present invention.

FIG. 17 shows a process for manufacturing a covered stent according to an embodiment of the present invention. Stent 1701 is mounted on a spinning mandrel 1702. Stent 1701 may be constructed using any of a variety of techniques and materials. An adhesion layer 1703 is created by pouring a thread of adhesion layer material 1704 onto mounted stent 1701. In one embodiment, adhesion layer material 1704 is in the liquid phase, but becomes partially or entirely solid phase once contact with stent 1701 is made. In a preferred embodiment, PLA is used as the adhesion layer material 1704, but many other materials are contemplated, such as biodegradable, dissolvable, non-biodegradable, and non-dissolvable materials. The thickness of an adhesion layer 1703 may be varied by changing the diameter of the application nozzle 1705, the speed at which application nozzle 1705 passes along the surface of stent 1701, the angle of the application along the axis, the amount of waviness to the application, or the number of passes made by application nozzle 1705. In one embodiment, the thickness of the adhesion layer is 0.05-1 mm, but other adhesion layer thicknesses are contemplated by the present invention. Multiple layers of material may be used to create adhesion layer 1703.

Figure 18:
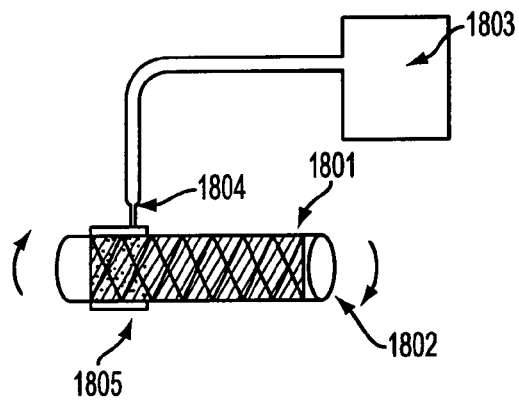
FIG. 18 shows a process for applying a stent cover over an adhesion layer.

FIG. 18 shows a process for applying a stent cover over an adhesion layer. Stent with applied adhesion layer 1801 is mounted on a spinning mandrel 1802. Stent cover material 1803 may be applied to stent 1801 through application nozzle 1804. Porosity of the stent cover 1805 may be varied by using different materials, application nozzles, application speeds, and other techniques. In one embodiment, a polyurethane layer may be sprayed onto the applied adhesion layer with application nozzle 1804 to form a non-permeable inner layer of a stent cover. A second, porous layer of polyurethane may then be applied by using a different application nozzle such that a spun polyurethane layer is formed. In other embodiments, an electrostatic spinning process may be employed. In this process, a voltage may be applied to the mandrel while the spinneret is grounded. The resulting electrostatic charge will help keep the material to be spun on the stent surface. In yet other embodiments, the number and characteristic of the stent cover layers may be varied; as well as the pore sizes created using this technique. In one embodiment, the outer stent cover 1805 layer may have a pore size in the range of 10-60 microns.

Figure 19:
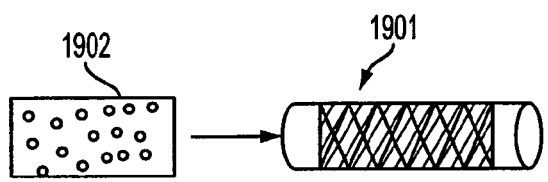
FIG. 19 shows an alternative process for applying a stent cover over an adhesion layer.

FIG. 19 shows an alternative process for applying a stent cover over an adhesion layer. Once a stent with an adhesion layer 1901 is created, for instance, according to the process described in FIG. 17 and the accompanying description, a preformed stent cover 1902 may be pulled over the stent 1901 to form a covered stent.

Figure 20:
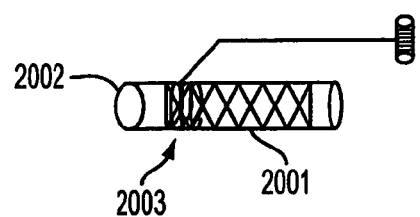
FIG. 20 shows an alternative design and fabrication process according to an embodiment of the invention.

FIG. 20 shows an alternative design and fabrication process according to an embodiment of the present invention. Stent 2001 is covered by an adhesion layer by immersing the stent 2001 in a container of adhesion layer material. Liquid adhesion materials may be used in a preferred embodiment of the present invention, but other forms such as slurries or gases may also be used. Stent 2001 is then placed on an arm 2002 of a spinning machine, the design of which is familiar to those skilled in the art. A stent cover layer 2003 is then spun onto the surface of the stent 2001, varying the spinning method such that the cover layer has variable porosity. For example, an inner layer of the stent cover 2003 may be of low porosity to minimize or avoid fluid or cell transference, while the outer layer may be of greater porosity to promote tissue ingrowth. In other embodiments, for example those illustrated in FIGS. 17-20, the porosity characteristics may vary. In a preferred embodiment, block copolymer may be used as the stent cover 2003 material, while PLA may be used as the material for an adhesion layer.

Although the present invention has been described with reference to preferred embodiments, those skilled in the art will recognize that changes can be made in form and detail without departing from the spirit and scope of the invention. It will be evident from considerations of the foregoing that the devices of the present invention may be constructed using a number of methods and materials, in a wide variety of sizes and styles for the greater efficiency and convenience of a user.

While the foregoing has described what are considered to be preferred embodiments of the invention, it is understood that various modifications may be made therein and that the invention may be implemented in various forms and embodiments, and that it may be applied in numerous applications, only some of which have been described herein. It is intended by the following claims to claim all such modifications and variations which fall within the true scope of the invention.

It should further be noted and understood that all publications, patents and patent applications mentioned in this specification are indicative of the level of skill of those skilled in the art to which the invention pertains. All publications, patents and patent applications are herein incorporated by reference to the same extent as if each individual publication patent or patent application was specifically and individually indicated to be incorporated by reference in its entirety.

What is claimed is:

1. A method of forming an implantable composite stent, the method comprising:
   depositing a liquid adhesive material onto an outer surface of a self-expandable mesh stent as the self-expandable mesh stent is being rotated;
   depositing cover material onto the adhesive material to form a covered stent, wherein the self-expandable mesh stent is rotating as the cover material is being applied;
   connecting a bioabsorbable mesh stent to an outer surface of the covered stent to form the composite stent, wherein the self-expandable stent forms an inner layer of the composite stent and the bioabsorbable mesh stent forms the outer layer of the composite stent; and
   attaching a retrieval loop element to the self-expandable stent, wherein a portion of the retrieval loop element is positioned between the cover material and the self-expandable stent after the cover material is applied to the self-expandable stent.

2. The method of claim 1, wherein the bioabsorbable stent is connected to the covered stent with a connection selected from the group consisting of fasteners; sutures; clips; staples; dissolvable gel, adhesive; mechanical interlock; interweaving with a degradable filament; and mating land and grooves of the bioabsorbable stent to lands and grooves of the stent.

3. The method of claim 1, wherein the bioabsorbable stent is connected to the covered stent by a bioabsorbable means selected from the group consisting of sutures; clips; staples; dissolvable gel, adhesives; dissolvable adhesives; and pH-reactive connectors.

4. The method of claim 1, wherein the liquid adhesive material becomes partially or entirely solid phase after deposition onto the outer surface of the self-expandable stent.

5. The method of claim 1, wherein depositing cover material comprises depositing a first cover material to form a non-porous layer and depositing a second cover material to form a porous layer.

6. The method of claim 5, wherein the porous layer has a pore size in the range of 10 to 60 microns.

7. The method of claim 6, wherein the porous layer forms an outer layer of cover material.

8. The method of claim 5, wherein the second cover material comprises polyurethane.

9. The method of claim 1, wherein the self-expandable stent forms an inner layer of the composite stent.

10. The method of claim 1, wherein depositing cover material comprises spraying a polyurethane layer onto the adhesive material and then applying a spun polyurethane layer onto the sprayed polyurethane layer, the spun polyurethane layer being more porous than the sprayed polyurethane layer.

11. The method of claim 10, wherein a first nozzle is used to spray the polyurethane layer and a second nozzle different from the first nozzle is used to apply the spun polyurethane layer.

12. The method of claim 1, wherein depositing cover material comprises an electrostatic spinning process.

13. The method of claim 1, wherein the bioabsorbable stent is detachably connected to the covered stent.

14. The method of claim 1, wherein the self-expandable stent is a metal stent.

15. The method of claim 1, wherein the bioabsorbable stent is a polymeric stent.

16. The method of claim 1, wherein the adhesive material is polylactide.

17. The method of claim 1, wherein the adhesive material has a thickness of 0.05 to 1 mm.

18. The method of claim 1, wherein the cover material comprises a block copolymer.